United States Patent
Motoike (10) Patent No.: US 10,421,828 B2
(45) Date of Patent: Sep. 24, 2019

(54) RESIN COMPOSITION FOR SOLID POLYMER FUEL CELL SEALING MATERIAL AND SOLID POLYMER FUEL CELL SEALING MATERIAL USING SAID RESIN COMPOSITION

(71) Applicant: PANAC Co., Ltd., Tokyo (JP)

(72) Inventor: Shingo Motoike, Fujinomiya (JP)

(73) Assignee: PANAC Co., Ltd., Tokyo (JP)

( * ) Notice: Subject to any disclaimer, the term of this patent is extended or adjusted under 35 U.S.C. 154(b) by 100 days.

(21) Appl. No.: 15/527,229

(22) PCT Filed: Nov. 17, 2015

(86) PCT No.: PCT/JP2015/082308
§ 371 (c)(1),
(2) Date: May 16, 2017

(87) PCT Pub. No.: WO2016/080409
PCT Pub. Date: May 26, 2016

(65) Prior Publication Data
US 2017/0335026 A1    Nov. 23, 2017

(30) Foreign Application Priority Data
Nov. 17, 2014   (JP) ................................. 2014-233154

(51) Int. Cl.
| | |
|---|---|
| H01M 8/0284 | (2016.01) |
| C08F 20/28 | (2006.01) |
| C08F 212/08 | (2006.01) |
| C08F 220/32 | (2006.01) |
| C08G 59/32 | (2006.01) |
| C08F 12/08 | (2006.01) |
| C08F 22/10 | (2006.01) |
| C08F 220/20 | (2006.01) |
| C07D 303/16 | (2006.01) |
| H01M 8/1018 | (2016.01) |

(52) U.S. Cl.
CPC .............. *C08F 20/28* (2013.01); *C08F 12/08* (2013.01); *C08F 22/105* (2013.01); *C08F 212/08* (2013.01); *C08F 220/20* (2013.01); *C08F 220/32* (2013.01); *C08G 59/32* (2013.01); *H01M 8/0284* (2013.01); *C07D 303/16* (2013.01); *C08F 2500/01* (2013.01); *H01M 2008/1095* (2013.01)

(58) Field of Classification Search
CPC .................................................... H01M 8/0284
See application file for complete search history.

(56) References Cited

U.S. PATENT DOCUMENTS

2006/0276592 A1*   12/2006   Kanae ................. C08L 23/0815
                                                     525/236

FOREIGN PATENT DOCUMENTS

| JP | H06-119930 A | 4/1994 |
|---|---|---|
| JP | 2000-56694 A | 2/2000 |
| JP | 2002-42835 A | 2/2002 |
| JP | 2004-247185 A | 9/2004 |
| JP | 2006-236671 A | 9/2006 |
| JP | 2008-171667 A | 7/2008 |
| JP | 2010-20964 A | 1/2010 |
| JP | 2010-232047 A | 10/2010 |
| JP | 2010-235656 A | 10/2010 |
| JP | 2011-012023 A | 1/2011 |
| JP | 2011-213767 A | 10/2011 |
| JP | 2015-2029 A | 1/2015 |
| WO | 2011/016492 A1 | 2/2011 |

OTHER PUBLICATIONS

International Search Report for PCT/JP2015/082308 dated Feb. 23, 2016; English translation submitted herewith (4 pages).

* cited by examiner

*Primary Examiner* — Wenwen Cai
(74) *Attorney, Agent, or Firm* — Fitch, Even, Tabin & Flannery, LLP (57) ABSTRACT

Provided is a resin composition for a solid polymer fuel cell sealing material, the resin composition including a copolymer resin having a weight average molecular weight of 150,000 or more and formed by copolymerizing raw material components including: (a1) 5% by mass or more of styrene; and (b) 20% by mass or less of glycidyl (meth)acrylate. Preferably, the raw material components are configured to further include (c) one or more kinds of other polymerizable monomers selected from a hydroxyalkyl (meth)acrylate and an alkyl (meth)acrylate.

19 Claims, 1 Drawing Sheet

RESIN COMPOSITION FOR SOLID POLYMER FUEL CELL SEALING MATERIAL AND SOLID POLYMER FUEL CELL SEALING MATERIAL USING SAID RESIN COMPOSITION

CROSS-REFERENCE TO RELATED APPLICATIONS

This application is a U.S. national phase application filed under 35 U.S.C. § 371 of International Application No. PCT/JP2015/082308, filed Nov. 17, 2015, designating the United States, and claims priority from Japanese Patent Application No. 2014-233154, filed Nov. 17, 2014, and the complete disclosures of which applications are hereby incorporated herein by reference in their entirety for all purposes.

TECHNICAL FIELD

The present invention relates to a resin composition for a solid polymer fuel cell sealing material and a solid polymer fuel cell sealing material using the resin composition.

BACKGROUND ART

A solid polymer fuel cell (hereinafter, may be referred to as "fuel cell") simultaneously generates electric power and heat by electrochemically reacting a fuel gas including hydrogen with an oxidant gas including oxygen.

Figure 1:
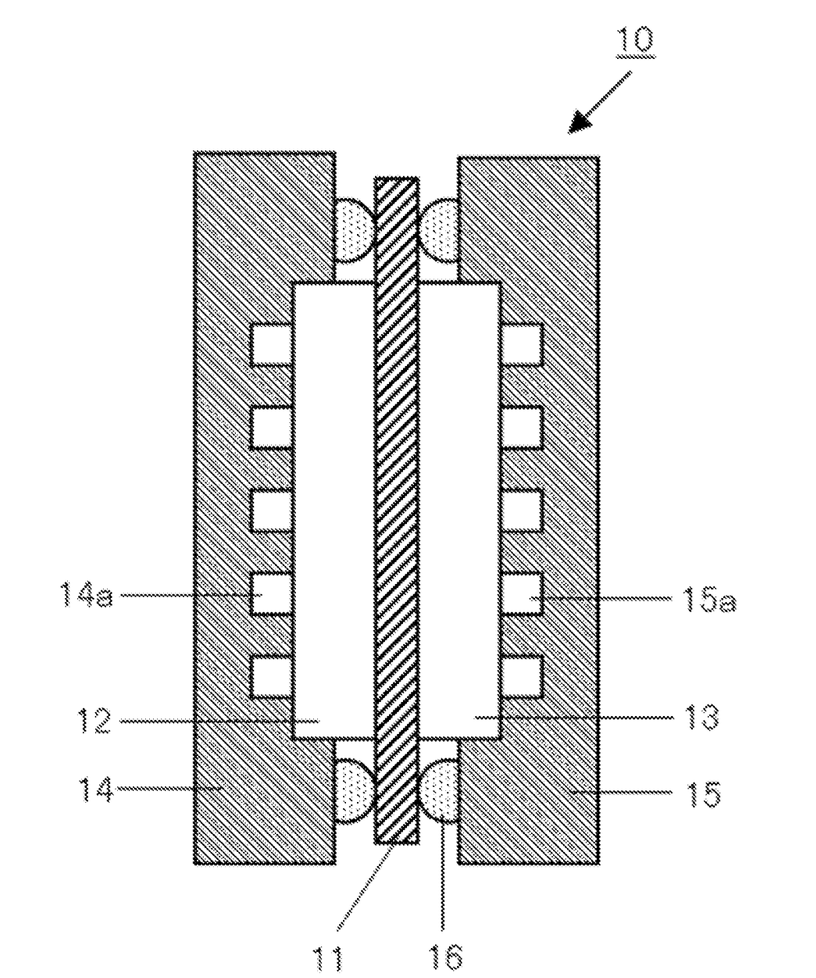
FIG. 1 is a cross-sectional view illustrating an example of a cell that constitutes a general fuel cell.

FIG. 1 illustrates a cross-sectional view of a cell 10, which is a constituent unit of a general fuel cell. A general fuel cell is configured such that several dozen to several hundred units of the cell 10 are laminated, the laminate is sandwiched between end plates, with a current collector plate and an insulating plate interposed therebetween, and these members are tightly fastened with fastening bolts from both ends.

A fuel cell configured as such is operated in a high-temperature high-humidity state, and a trace amount of hydrofluoric acid is eluted from a solid polymer electrolyte membrane (hereinafter, may be referred to as "electrolyte membrane"). Therefore, in order to enable fuel cells to endure such conditions, a sealing material 16 is required to have heat resistance, hot water resistance, and acid resistance.

Regarding such a sealing material, the means of PTL 1 to PTL 5 have been suggested.

CITATION LIST

Patent Literature

PTL 1: JP 6-119930 A
PTL 2: JP 2010-20964 A
PTL 3: JP 2002-42835 A
PTL 4: JP 2000-56694 A
PTL 5: JP 2008-171667 A

SUMMARY OF INVENTION

Technical Problem

PTL 1 describes the use of an O-ring as a sealing material. However, the invention of PTL 1 has a problem that it is necessary to process a separator to form a groove for inserting an O-ring, thickness reduction is difficult due to the structure, a large clamping capacity is needed, and the separator is damaged by the force of this clamping capacity.

The inventions of PTL 2 to PTL 5 do not have such a problem as described above because the inventions do not use an O-ring. However, the inventions have the following problems.

In PTL 2, it is described that alkali metal-containing amorphous silica particles having their carbon content C/Si decreased by a decarbonization treatment are used as a sealing material. However, the sealing material of PTL 2 has a very high fusion temperature such as 770° C. or higher, requires large-sized heating facilities for the sealing operation, and lacks general-purpose usability.

In PTL 3, it is described that a urethane-based resin or a liquid silicone rubber is used as a sealing material. However, urethane resins have a problem that the resins undergo hydrolysis in a high-humidity environment. Also, polyurethane resins are broadly classified into polyester-based resins and polyether-based resins; however, they are all easily affected by heat, and the adhesive force of polyester-based resins is decreased at a temperature below 100° C., while the adhesive force of polyether-based resins is decreased at about 70° C. Liquid silicone rubbers have a problem that the materials have low mechanical strength and are easily subjected to hydrolysis in the presence of acid, alkali, or the like.

In PTL 4, it is described that an olefin-based resin, a soft epoxy-based resin, or the like is used as a sealing material. However, olefin resins undergo a decrease in the cohesive force of the resin in a high-temperature environment, and therefore, sufficient adhesive force may not be obtained. Soft epoxy-based resins have a problem that the adhesive force is decreased as a result of softening in a high-temperature environment.

In PTL 5, it is described that a composition including a styrene-based block polymerized elastomer and a tackifier is used as a sealing material. However, the composition undergoes a decrease in the adhesive force in a high-temperature environment.

Furthermore, these sealing materials do not easily adhere in a case in which the adherend (for example, a gas flow channel) is constructed from a resin having low surface polarity.

An object of the present invention is to provide a resin composition for a solid polymer fuel cell sealing material, the resin composition having high adhesiveness even to non-polar materials and exhibiting suppressed decrease in the adhesive force in a high-temperature environment, with moisture-induced deterioration of the resin composition being prevented; and a solid polymer fuel cell sealing material with suppressed detachment and deterioration, the sealing material using the aforementioned resin composition.

Solution to Problem

The resin composition for a solid polymer fuel cell sealing material of the present invention, a solid polymer fuel cell sealing material, which uses the resin composition, and a solid polymer fuel cell using the sealing material are as described in the following items [1] to [7].

[1] A resin composition for a solid polymer fuel cell sealing material, the resin composition comprising a copolymer resin having a weight average molecular weight of 150,000 or more and formed by copolymerizing raw material components including: (a1) 5% by mass or more of styrene and (b) 20% by mass or less of glycidyl (meth)acrylate.

[2] The resin composition for a solid polymer fuel cell sealing material according to [1], wherein the raw material components further include (a2) 5% by mass or more of methyl methacrylate.

[3] The resin composition for a solid polymer fuel cell sealing material according to [1] or [2], wherein the content of glycidyl (meth)acrylate in the copolymer resin is 0.007 to 1.05 eq/kg. [4] The resin composition for a solid polymer fuel cell sealing material according to any one of [1] to [3], wherein the raw material components further include (c) one or more kinds of other polymerizable monomers selected from a hydroxyalkyl (meth)acrylate and an alkyl (meth) acrylate.

[5] The resin composition for a solid polymer fuel cell sealing material according to any one of [1] to [4], wherein the resin composition further includes a curing agent having a functional group capable of reacting with a glycidyl group.

[6] A solid polymer fuel cell sealing material being formed from the resin composition according to any one of [1] to [5].

[7] A solid polymer fuel cell sealing material comprising: a sheet-like sealing material layer formed from the resin composition according to any one of [1] to [5]; and peelable base materials respectively disposed on either surface of the sealing material layer to sandwich the sealing material layer.

In the following description, the resin composition for a solid polymer fuel cell sealing material of the present invention may be referred to as "resin composition of the present invention", and the solid polymer fuel cell sealing material using the resin composition of the present invention may be referred to as "sealing material of the present invention".

Advantageous Effects of Invention

The resin composition and sealing material of the present invention have high adhesiveness even for non-polar materials, and exhibit suppressed decrease in the adhesive force in a high-temperature environment, while being capable of preventing moisture-induced deterioration. Therefore, the resin composition and the sealing material can stabilize the performance of a fuel cell over time.

DESCRIPTION OF EMBODIMENTS

[1] Resin composition for solid polymer fuel cell sealing material

The resin composition of the present invention includes a copolymer resin having a weight average molecular weight (Mw) of 150,000 or more and formed by copolymerizing raw material components including: (a1) 5% by mass or more of styrene, and (b) 20% by mass or less of glycidyl (meth)acrylate.

According to the present invention, the weight average molecular weight (Mw) is a value measured by gel permeation chromatography and calculated relative to polystyrene standards.

Furthermore, (a1) styrene and (a2) methyl methacrylate may be collectively referred to as component (a); (b) glycidyl (meth)acrylate may be referred to as component (b); and (c) a hydroxyalkyl (meth)acrylate and an alkyl (meth) acrylate may be referred to as component (c).

(a) Component (a1) Styrene (styrene monomer) is included in the raw material components in an amount of 5% by mass or more.

Since styrene is a non-polar component having constituent elements consisting of C and H, when styrene is introduced in an amount of 5% by mass or more into the copolymer resin according to the present invention that becomes an epoxy group-containing acrylic rubber due to the presence of component (b), excellent adhesiveness and adherence can be imparted between a polar material (for example, an electrolyte membrane) and a constructed article of a non-polar material.

Furthermore, since styrene has a relatively high glass transition temperature (Tg), when styrene is introduced into the copolymer resin according to the present invention, heat-resistant adhesiveness induced by a cohesive force enhancing effect is also obtained.

In many of general techniques for imparting the function of heat-resistant adhesiveness to a copolymer resin, adhesiveness is imparted to the resin by incorporating a silane coupling agent, a tackifier, and the like; however, there are occasions in which exudation (bleed-out) of a silane coupling occurs and impairs reliability of manufactured products. However, the risk of bleed-out is eliminated by incorporating styrene into the resin itself as a copolymerization component.

Determination of whether a component or a material is non-polar is carried out by checking whether the SP value of the component or the material is less than 20 (preferably 19 or less; and more preferably 18 or less). For example, examples of a non-polar material include a polystyrene resin (PS), a polyphenylene ether resin (PPO), polypropylene (PP), and polyethylene (PE), and the respective SP values thereof are 18.0 for PS, 18.0 for PPO, 17.0 for PP, and 16.4 for PE. There are no particular limitations on the lower limit of the SP value of the component or material; however, the sealing material of the present invention can be suitably used for a non-polar material generally having a SP value of 16 or higher.

Regarding the method for calculating the SP value, a method of estimating the SP value from a calculation formula used in the Novel method for converting PVT data into CED data; a method of calculating the SP value based on the components with known SP values, and the like are known. For example, reference can be made to the tables listed in the webpage of the Japan Engineering Plastics Technical Committee (http://www.enplajp/book/seigo/P27.pdf).

It is preferable that the sealing material of the present invention has a hardness that conforms to the shape of the adherend to some extent. From such a point of view, it is preferable that the content of styrene in the raw material components is adjusted to a value of 50% by mass or less. When the content of styrene in the raw material components is set to a value of 50% by mass or less, the proportion of (b) glycidyl (meth)acrylate that will be described below can be secured, the decrease in the adhesive force in a high-temperature environment can be further suppressed, and also, more satisfactory acid resistance can be obtained.

The content of styrene in the raw material components is preferably 5% by mass or more and less than 40% by mass, and even more preferably 7% by mass or more and 30% by mass or less.

(a2) Methyl methacrylate

It is preferable that the raw material components further include (a2) methyl methacrylate as the component (a).

It is preferable that the (a2) methyl methacrylate (methyl methacrylate monomer) is included in the raw material components of the copolymer resin at a proportion of 5% by mass or more. When methyl methacrylate is used together with styrene, the glass transition temperature (Tg) of the copolymer resin obtainable by copolymerizing the raw material components can be finely adjusted. Also, since the weight average molecular weight can be adjusted, adhesiveness between materials having different polarities, and the bonding conditions can be controlled.

Furthermore, when the raw material components include methyl methacrylate, decomposition of the copolymer resin caused by moisture and acid and consequent reduction of the weight of the resin can be prevented, and also, decrease in the adhesive force in a high-temperature environment can be suppressed. Furthermore, when the raw material components include methyl methacrylate at a proportion of 5% by mass or more, the softening point of the copolymer resin can be elevated, and satisfactory handleability can be obtained when the copolymer resin as a sealing material.

It is preferable that the total amount of the component (a) [sum total of (a1) styrene and (a2) methyl methacrylate] is adjusted to a value of 50% by mass or less in the raw material components of the copolymer resin. When the total amount of the component (a) is adjusted to a value of 50% by mass or less, the proportion of (b) glycidyl (meth)acrylate that will be described below can be secured, decrease in the adhesive force in a high-temperature environment can be further suppressed, and more satisfactory acid resistance can be obtained.

The total amount of the component (a) is more preferably 20% by mass or more and 50% by mass or less, and even more preferably 25% by mass or more and less than 40% by mass.

(b) Glycidyl (meth)acrylate

Glycidyl (meth)acrylate (glycidyl (meth)acrylate monomer) is included at a proportion of 20% by mass or less in the raw material components of the copolymer resin. When the copolymer resin includes glycidyl (meth)acrylate, the cohesive force of the resin can be secured while the adhesive force in a high-temperature environment is maintained. Also, when the content proportion of glycidyl (meth)acrylate is adjusted to a value of 20% by mass or less, gelation of the copolymer resin can be prevented, and also, an effect of suppressing deterioration caused by moisture and acid can be further enhanced by securing the proportion of the component (a).

The content proportion of glycidyl (meth)acrylate is preferably 0.1% to 15% by mass, more preferably 0.5% to 10.0% by mass, and even more preferably 1.0% to 5.0% by mass.

Regarding glycidyl (meth)acrylate, any one of glycidyl methacrylate and glycidyl acrylate can be used; however, from the viewpoints of handleability such as skin irritancy, stability of the compound, and ease of synthesis, glycidyl methacrylate is suitable.

(c) Other polymerizable monomer

It is preferable that the copolymer resin includes one or more kinds of other polymerizable monomers selected from a hydroxyalkyl (meth)acrylate and an alkyl (meth)acrylate in the raw material components.

When the copolymer resin includes the component (a), deterioration caused by moisture and acid can be suppressed, and satisfactory adhesive force in a high-temperature environment can be obtained. However, the softening point of the copolymer resin may be elevated too high. Here, when the copolymer resin includes another polymerizable monomer of the component (c), the softening point of the copolymer resin is lowered, and workability can be enhanced when the sealing material at the sealed site of the cells of a fuel cell is thermally fused.

Examples of the hydroxyalkyl (meth)acrylate include 2-hydroxyethyl (meth)acrylate and 4-hydroxybutyl (meth)acrylate.

Regarding the alkyl (meth)acrylate, an alkyl (meth)acrylate other than methyl methacrylate can be used, and examples include butyl (meth)acrylates such as n-butyl (meth)acrylate, isobutyl (meth)acrylate, sec-butyl (meth)acrylate, and tert-butyl (meth) acrylate; ethyl (meth)acrylate, pentyl (meth) acrylate, isopentyl (meth) acrylate, hexyl (meth)acrylate, cyclohexyl (meth) acrylate, heptyl (meth) acrylate, octyl (meth)acrylate, isooctyl (meth)acrylate, 2-ethylhexyl (meth) acrylate, nonyl (meth) acrylate, isononyl (meth) acrylate, decyl (meth) acrylate, dodecyl (meth) acrylate, and tridecyl (meth)acrylate.

Regarding the other polymerizable monomer, an alkyl (meth)acrylate is suitable from the viewpoint of hot water resistance. Furthermore, from the viewpoint that the softening point of the copolymer resin can be easily adjusted, an alkyl acrylate is suitable. Furthermore, from the viewpoint of being easily copolymerizable and having industrially general-purpose usability, butyl acrylate or ethyl acrylate is suitable. Also, from the viewpoint of adjusting the softening point, it is also suitable to use butyl acrylate and ethyl acrylate in combination.

It is preferable that the other polymerizable monomer is included at a proportion of 5% by mass or more and less than 80% by mass, more preferably 15% to 70% by mass, and even more preferably 25% to 60% by mass, in the raw material components of the copolymer resin. When the content of the other polymerizable monomer is adjusted to a value of 5% by mass or more, the softening point of the copolymer resin is lowered, and the thermal fusion operation of the sealing material can be performed easily. When the content of the other polymerizable monomer is adjusted to a value of less than 80% by mass, the proportions of methyl methacrylate and glycidyl (meth)acrylate can be secured, and the adhesive force in a high-temperature environment, hot water resistance, and acid resistance can be improved.

The copolymer resin is obtained by copolymerizing a raw material composition that includes the component (a) including at least (a1) styrene; and the (b) glycidyl (meth)acrylate described above, and optionally includes (c) another polymerizable monomer that is used as necessary.

Examples of the method for copolymerization include suspension polymerization, emulsion polymerization, solution polymerization, and the like. Among these methods for copolymerization, suspension polymerization is suitable from the viewpoint that a polymer having a narrow molecular weight distribution and having a reduced amount of residual monomers is obtained, from the viewpoint that high molecular mass polymer is obtained, from the viewpoint that the product has a reduced amount of impurities because an emulsifier is unnecessary, and from the viewpoint that while polymerization is carried out in water, a copolymer resin having excellent water resistance and heat resistance is easily obtained.

Regarding the polymerization conditions, for example, in the case of suspension polymerization, it is preferable that polymerization is performed at 50° C. to 80° C. for 2 to 24 hours.

The form of the copolymer may be any of an alternating form, a random form, a block form, a graft form, and the like.

In regard to water-based suspension polymerization for producing a particulate body, one or more kinds of suspension stabilizers can be used. Examples thereof include water-soluble polymers such as polyvinyl alcohol, a partially saponified polyvinyl alcohol, polyvinylpyrrolidone, a (meth)acrylic acid salt, polyacrylamide, a partially saponified polyacrylamide, carboxymethyl cellulose, methyl cellulose, ethyl cellulose, and the like; inorganic salt powders such as calcium phosphates, calcium carbonate, and the like; and the like.

The polymerization initiator is preferably such that the polymerization initiating radical species obtainable after decomposition is oil-soluble.

Typical examples of the radical polymerization initiator include an azo-based radical polymerization initiator and a peroxide-based radical polymerization initiator.

Examples of the azo-based radical polymerization initiator include 2,2'-azobispropane, 2,2'-dichloro-2,2'-azobispropane, 1,1'-azo(methylethyl) diacetate, 2,2'-azobis(2-amidinopropane) hydrochloride, 2,2'-azobis(2-aminopropane) nitrate, 2,2'-azobisisobutane, 2,2'-azobisisobutylamide, 2,2'-azobisisobutyronitrile, methyl 2,2'-azobis-2-methylpropionate, 2,2'-dichloro-2,2'-azobisbutane, 2,2'-azobis-2-methylbutyronitrile, dimethyl 2,2'-azobisisobutyrate, 1,1'-azobis (sodium 1-methylbutyronitrile-3-sulfonate), 2-(4-methylphenylazo)-2-methylmalonodinitrile, 4,4'-azobis-4-cyanovaleric acid, 3,5-dihydroxymethylphenylazo-2-allylmalonodinitrile, 2,2'-azobis-2-methylvaleronitrile, dimethyl 4,4'-azobis-4-cyanovalerate, 2,2'-azobis-2,4'-dimethylvaleronitrile, 1,1'-azobiscyclohexanenitrile, 2,2'-azobis-2-propylbutyronitrile, 1,1'-azobiscyclohexanenitrile, 2,2'-azobis-2-propylbutyronitrile, 1,1'-azobis-1-chlorophenylethane, 1,1'-azobis-1-cyclohexanecarbonitrile, 1,1'-azobis-1-cycloheptanenitrile, 1,1'-azobis-1-phenylmethane, 1,1'-azobiscumene, ethyl 4-nitrophenylazobenzylcyanoacetate, phenylazodiphenylmethane, phenylazotriphenylmethane, 4-nitrophenylazotriphenylmethane, 1,1'-azobis-1,2-diphenylethane, poly(bisphenol A-4,4'-azobis-4-cyanopentanoate), and poly(tetraethylene glycol-2,2' azobisisobutyrate).

Examples of the peroxide-based radical polymerization initiator include acetyl peroxide, cumyl peroxide, tert-butyl peroxide, propionyl peroxide, benzoyl peroxide, 2-chlorobenzoyl peroxide, 3-chlorobenzoyl peroxide, 4-chlorobenzoyl peroxide, 2,4-dichlorobenzoyl peroxide, 4-bromomethylbenzoyl peroxide, lauroyl peroxide, potassium persulfate, diisopropyl peroxycarbonate, tetralin hydroperoxide, 1-phenyl-2-methylpropyl-1-hydroperoxide, tert-butyl triphenylperacetate, tert-butyl hydroperoxide, tert-butyl performate, tert-butyl peracetate, tert-butyl benzoate, tert-butyl phenylperacetate, tert-butyl 4-methoxyperacetate, and tert-butyl N-(3-toluyl)percarbamate. Examples of the polymerization initiator include peroxides such as benzoyl peroxide, lauroyl peroxide, cumene hydroperoxide, t-butyl hydroperoxide, di-t-butyl peroxide, and methyl ethyl ketone peroxide.

Furthermore, a mercapto compound can be added as a chain transfer agent. Examples thereof include chain transfer agents having hyroxyl groups, such as mercaptoethanol, mercaptopropanol, mercaptobutanol, mercaptopropanediol, mercaptobutanediol, hydroxybenzenethiol, and derivatives thereof 1-butanethiol, butyl-3-mercaptopropionate, methyl-3-mercaptopropionate, 2,2-(ethylenedioxy)diethanethiol, ethanethiol, 4-methylbenzenethiol, dodecylmercaptane, propanethiol, butanethiol, pentanethiol, 1-octanethiol, cyclopentanethiol, cyclohexanethiol, thioglycerol, 4,4-thiobisbenzenethiol, and the like.

The weight average molecular weight of the copolymer resin is 150,000 or more. When the weight average molecular weight is adjusted to a value of 150,000 or more, satisfactory adhesive force in a high-temperature environment can be obtained. It is preferable that the weight average molecular weight of the copolymer resin is adjusted to a value of 1,500,000 or less from the viewpoint of suppressing gelation at the time of polymerization and stabilizing the product quality. The weight average molecular weight of the copolymer resin is preferably 400,000 to 1,000,000, and more preferably 500,000 to 800,000.

The primary softening point of the copolymer resin is preferably 80° C. to 150° C., and more preferably 100° C. to 140° C. When the softening point is adjusted to a temperature of 100° C. or higher, adhesiveness can be secured in a high-temperature environment, and when the softening point is adjusted to a temperature 150° C. or lower, fluidity can be secured at the time of bonding by hot pressing or the like. The softening point can be measured by the method described in the Examples.

The epoxy equivalent of the copolymer resin is preferably 710 to 1,430,000 g/eq, more preferably 950 to 143,000 g/eq, even more preferably 1,420-28,600 g/eq, and still more preferably 2,840-14,300 g/eq. When the epoxy equivalent is adjusted to a value of 1,430,000 g/eq or less, adhesiveness can be secured in a high-temperature environment, and when the epoxy equivalent is adjusted to a value of 710 g/eq or more, the cohesive force of the resin can be increased while having the adhesiveness in a high-temperature environment secured. The epoxy equivalent can be measured by titration.

Furthermore, the glycidyl (meth)acrylate content (GMA content) of the copolymer resin is preferably 0.007 to 1.05 eq/kg, more preferably 0.035 to 0.70 eq/kg, and even more preferably 0.07 to 0.35 eq/kg.

The GMA content is calculated as follows.

For example, if it is said that the resin composition includes 1% by mass of glycidyl (meth)acrylate (GMA), this is 0.01/142 (GMA molecular weight)=0.00007 [mol/g], and when this is converted to the equivalent unit, the GMA content becomes 0.07 [eq/kg].

In order to make it easy to sufficiently exhibit the effects of the present invention, it is preferable that the copolymer resin is included at a proportion of 50% by mass or more, more preferably at a proportion of 60% by mass or more, even more preferably at a proportion of 80% by mass or more, and still more preferably at a proportion of 90% by mass or more, of the total solid content of the resin composition of the present invention.

(Curing Agent Having Functional Group Capable of Reacting with Glycidyl Group)

The resin composition of the present invention may include a curing agent having a functional group that is capable of reacting with a glycidyl group (hereinafter, may be referred to as "glycidyl curing agent"). When the resin composition includes a glycidyl curing agent, decrease in the adhesive force in a high-temperature environment can be suppressed, deterioration of the resin composition in a high-temperature environment and consequent reduction of weight can be prevented, and the performance of the fuel cell can be stably retained.

Regarding the glycidyl curing agent, polyamine, polyphenol, an acid anhydride, polysulfide, boron trifluoride, and the like are suitably used.

Examples of a polyamine include 4,4'-diaminodiphenylmethane, 4,4'-diaminodiphenylsulfone, meta-phenylenediamine, 4,4'-diamino-3,3'-diethyl-5,5'-di-4,4'-dimethyldiphenylmethane, 3,3'-dimethoxy-4,4'-diaminodiphenyl, 3,3'- dimethyl-4,4'-di-4,4'-diaminodiphenyl, 2,2'-dichloro-4,4'-diamino-5,5'-dimethoxydimethyl, 2,2',5,5'-tetrachloro-4,4'-diaminodiphenyl, 4,4'-dimethylenebis(2-chloroaniline), 2,2',3,3'-tetrachloro-4,4'-diaminodiphenylmethane, 4,4'-diaminodiphenyl ether, 4,4'-diaminobenzanilide, 3,3'-dihydroxy-4,4'-diaminobiphenyl, 9,9'-dibis(4-aminophenyl)fluorene, 9,9'-dibis(4-aminophenyl)anthracene, ethylenediamine, diethylaminopropylamine, hexamethylenediamine, isophoronediamine, bis(4-amino-3-methylcyclohexyl)methane, and the like.

Examples of a polyphenol include phenol novolac, o-cresol novolac, p-cresol novolac, p-t-butylphenol novolac, hydroxynaphthalene novolac, bisphenol A novolac, bisphenol F novolac, terpene-modified phenol, terpene-modified novolac, dicyclopentadiene-modified novolac, para-xylene-modified novolac, polybutadiene-modified phenol, and the like.

Examples of an acid anhydride include tetrahydrophthalic anhydride, methyltetrahydrophthalic anhydride, hexahydrophthalic anhydride, methylhexahydrophthalic anhydride, succinic anhydride, nadic anhydride, chlorendic anhydride, and the like.

Among the glycidyl curing agents, a polyphenol is suitable from the viewpoint of preventing elution of ammonium ions. Particularly, terpene-modified phenol is suitable from the viewpoint that this compound not only suppresses decrease in the adhesive force in a high-temperature environment, but is also capable of increasing the adhesive force in a high-temperature environment.

In a case in which a glycidyl curing agent is used, it is preferable that the glycidyl curing agent is included at a proportion of 0.1% by mass or more of the total solid content of the resin composition of the present invention. When the glycidyl curing agent is included at a proportion of 0.1% by mass or more, adhesiveness in a high-temperature environment can be maintained, and also, deterioration of the resin composition in a high-temperature environment and consequent reduction of the weight of the resin can be easily prevented. On the other hand, if the amount of the glycidyl curing agent is too large, the glycidyl curing agent itself may be eluted under the effect of heat, acid, or the like. Therefore, the content of the glycidyl curing agent is more preferably 0.5% to 50% by mass, even more preferably 1% to 20% by mass, and still more preferably 2% to 10% by mass.

In a case in which a glycidyl curing agent is used in addition to the copolymer resin, it is preferable that the glycidyl curing agent is mixed with the copolymer resin, and then the mixture is heated under the conditions of 100° C. to 170° C. for about 1 to 5 minutes.

(Other Additives)

The resin composition of the present invention may include additives such as a pigment, a flame retardant, an ultraviolet absorber, an oxidation inhibitor, an antistatic agent, a silane coupling agent, a tackifier, or the like, to the extent that the effects of the present invention are not impaired.

The resin composition of the present invention is preferably such that the elution amount of the ammonium ions included in the total solid content of the resin composition is 1 ppm/g or less on a mass basis. When the elution amount of ammonium ions is adjusted to a value of 1 ppm/g or less, elution of cations from the sealing material can be prevented, and the eluted cations can be prevented from affecting the performance of the fuel cell. The elution amount of ammonium ions in the copolymer resin is more preferably 1 ppm/g or less, and it is even more preferable that the resin composition does not include ammonium ions.

Usually, a resin having glycidyl groups is used in combination with an amine-based curing agent; however, in the present invention, it is preferable not to use an amine-based curing agent in order to suppress the amount of nitrogen atoms.

The amount of nitrogen atoms in the copolymer resin can be measured using, for example, an ion chromatography apparatus such as HIC-SP manufactured by SHIMADZU CORPORATION.

[Solid Polymer Fuel Cell Sealing Material]

The sealing material of the present invention is formed from the resin composition of the invention described above. The form of the sealing material is preferably a solid form such as a particulate form or a sheet-like form.

In regard to the sealing material of the present invention, from the viewpoint of handleability, a form in which a sheet-like sealing material layer formed from the resin composition of the present invention described above is sandwiched between peelable base materials that are respectively attached to either surface of the sealing material layer, is suitable.

In a case in which the sealing material is formed into a sheet-like form, the thickness of the sealing material layer may vary depending on the separator, the electrolyte membrane and the like of the fuel cell, and thus it cannot be generally mentioned; however, the thickness is preferably 10 to 500 μm, and more preferably 20 to 200 μm. Meanwhile, the sealing material layer may also be laminated, if necessary.

Regarding the peelable base material, a product obtained by subjecting a plastic film of polyethylene terephthalate, polybutylene terephthalate, polyethylene naphthalate, polycarbonate, polyethylene, polypropylene, polystyrene, triacetyl cellulose, poly(meth)acrylate, or polyvinyl chloride; paper; or the like, to a release treatment, is suitably used.

From the viewpoint of handleability, the peelable base material is preferably 10 to 100 μm, and more preferably 25 to 75 μm. The peelable base material is preferably a non-silicone-based base material, in order to prevent any adverse influence caused by migration of silicone components to the electrolyte membrane and the sealing material layer. The non-silicone-based peelable base material may be a base material having the surface treated with a polyolefin.

The sealing material of the present invention is such that, in order to suppress moisture-induced deterioration of the sealing material, the percentage of water content under the conditions in which the sealing material has been heated to 150° C. for 10 minutes, is preferably 1% by mass or less, more preferably 0.5% by mass, and even more preferably 0.3% by mass or less.

In a case in which the sealing material of the present invention is used as, for example, a sealing material for a fuel cell, when the percentage of water content of the sealing material is 1% by mass or less, a decrease in the power generation efficiency of the fuel cell can be suppressed. A sealing material for a fuel cell is required to have a performance that does not permeate hydrogen and oxygen that serve as fuel, from the viewpoint of the power generation efficiency and durability. Thus, moisture is likely to affect the fuel cell significantly. When the water content of the sealing material is a low water content (1% by mass or less), it is speculated that since water penetrates into the voids (passage of gases), gas permeation is suppressed.

The percentage of water content of the sealing material can be measured using, for example, a Karl Fischer moisture meter such as AQV-7 manufactured by HIRANUMA SANGYO Co., Ltd.

As described above, it is preferable that the sealing material of the present invention has a hardness that conforms to the shape of the adherend to some extent.

The strength of the resin composition that constitutes the sealing material can be estimated from the Tg of the copolymer resin included in the resin composition, and the bulk performance can be predicted. Strength can also be specifically digitized from Young's modulus based on a tensile test, and the bulk performance can be evaluated.

Strength of the simple form of the material is also important; however, on the occasion of adhesion, strength of the sealing material surface is also important. In a case in which a resin composition is obtained by mixing the copolymer resin with a curing agent, additives and the like, information on dispersibility of the curing agent, additives and the like into the copolymer resin are also obtained from the continuous hardness information from the sealing material surface layer.

These physical properties can be measured using, for example, a dynamic ultramicro hardness meter such as DUH-211 manufactured by SHIMADZU CORPORATION.

The hardness as used herein is surface microhardness determined not by a method of determining the diagonal length of an indentation, such as in the case of Vicker's hardness that is widely used for the measurement of hardness of a metallic material or the like, but by a method of measuring the extent to which an indenter has penetrated into a sample.

A diamond indenter is forced into a sample under a very low load, the depth of penetration of the indenter is continuously measured using a high resolution displacement meter, and the mechanical characteristics (adequate strength and conformity) of the material surface are evaluated.

For example, hardness of the sealing material of the present invention can be measured based on the indentation depth and the elastic modulus. The details of the measurement methods will be described in Examples. The indentation depth is the depth (μm) of a needle forced into the sealing material when the needle is pressed with a particular force (state in which a load of 0.5 mN is being applied to the sample).

The indentation depth of the sealing material is preferably 0.25 μm to 15 μm. When the depth is 0.25 μm or more, the sealing material can easily conform to the shape of an adherend, and when the depth is 15 μm or less, the sealing material has appropriate strength. The indentation depth of the sealing material is more preferably 0.5 μm to 12.5 μm, and even more preferably 1.0 μm to 10.0 μm.

The elastic modulus of the sealing material is preferably $4.0 \times 10^6$ Pa to $6.0 \times 10^8$ Pa. When the elastic modulus is $4.0 \times 10^6$ Pa or more, the sealing material can easily conform to the shape of an adherend, and when the elastic modulus is $6.0 \times 10^8$ Pa or less, the sealing material has appropriate strength. The elastic modulus of the sealing material is more preferably $6.0 \times 10^6$ Pa to $4.0 \times 10^8$ Pa, and even more preferably $8.0 \times 10^6$ Pa to $2.0 \times 10^8$ Pa.

The indentation depth and the elastic modulus of the sealing material are measured by the methods described in Examples.

Such sealing material of the present invention can be used at the sealing site of a fuel cell, and more specifically, at the sealing site of cells that constitute a fuel cell. At the time of use, the sealing material is heated and melted, and the sealing site of a cell is sealed with the molten sealing material. When a sealing material in which a sealing material layer is sandwiched between peelable base materials is used, the sealing material layer is heated and melted after the base materials are peeled off, and then the sealing site of a cell may be sealed with the molten sealing material layer.

[Solid Polymer Fuel Cell]

FIG. 1 is a cross-sectional view illustrating an example of a cell that constitutes a general fuel cell.

The cell 10 is configured to include a composite (MEA: Membrane and Electrode Assembly) composed of a solid polymer electrolyte membrane 11 and a pair of electrodes (anode and cathode) 12 and 13 respectively disposed on either surface of the electrolyte membrane; separators (14, 15) respectively disposed on either surface of the composite and having formed therein gas flow channels (14a, 15a) for respectively supplying a fuel gas and an oxidant gas; and a sealing material 16 for sealing the composite and the separators (14, 15) so as to tightly seal the gaps between the composite and the separators.

A general fuel cell is constructed by laminating several dozen to several hundred units of the cell 10; sandwiching the laminate between end plates, with a current collector and an insulating plate being interposed therebetween; and tightly fastening these members with fastening bolts from the end plates.

The sealing material of the present invention can be suitably used as a sealing material for such a general fuel cell. The position of the sealing material (sealing site) shown in FIG. 1 is only an example, and the position of the sealing material can be appropriately changed depending on the configuration of the cell that constitutes a fuel cell.

EXAMPLES

Hereinafter, the present invention will be specifically described by way of Examples; however, the present invention is not intended to be limited to the following examples.

The resin compositions for fuel cell sealing materials obtained in the following Examples and Comparative Examples were evaluated as described below.

<Adhesive Force (Room Temperature, 80° C.)>

A sealing material obtained in each of Examples and Comparative Examples and having a size of 1 cm×5 cm was sandwiched between a modified polyphenylene ether (m-PPE) resin sheet (thickness 0.2 mm) as a non-polar material having a size of 5 cm×5 cm and an electrolyte membrane (manufactured by DuPont Co., NAFION NRE-212, thickness 50 μm), and the assembly was press-bonded for 1 minute under the conditions of 5 MPa and 150° C. After the press-bonding, the resultant was cut into short strips each having a width of 1.5 cm, and thereby a plurality of samples A was obtained.

The m-PPE resin is an amorphous blend formed from a polyphenylene ether resin (PPO) and a polystyrene resin (PS), and has a SP value of 18.0.

[1. Initial Adhesive Force]

Each of the samples A was left to stand for one minute in an atmosphere at room temperature or at 80° C., and then the electrolyte membrane that had been reinforced using a polyimide tape over the entire surface of the electrolyte membrane side face was pulled with a Tensilon under the conditions of an angle of 180° and a speed of 10 mm/min. Thus, the peeling strength was measured. Meanwhile, the thickness of the sealing materials of Examples 1 to 9 and Comparative Examples 1 to 3 was set to 30 μm. The results are presented in Table 2.

In Example 1, the same measurement was also performed under the conditions of "leaving the sample A to stand for one minute in an atmosphere at room temperature" and under the conditions of "leaving the sample A to stand for one minute in an atmosphere at 80° C.".

[2. Adhesive Force After Enduring Hot Water]

(Hot Water Durability Treatment)

A sample A and water were introduced into a heat-resistant vessel, and the sample A was immersed therein. Next, the sample A was introduced into a thermostatic tank (dryer) at 95° C., and after a lapse of 100 hours, the sample A was removed from the thermostatic tank (dryer). Subsequently, moisture on the surface of the sample was wiped off, and thus a plurality of samples B was obtained.

Each of the samples B was left to stand for one minute in an atmosphere at room temperature or at 80° C., and then the sample B was reinforced with a polyimide tape over the entire surface of the electrolyte membrane side face. The polyimide tape and the electrolyte membrane were pulled with a Tensilon under the conditions of an angle of 180° C. and a speed of 10 mm/min, and thus the peeling strength was measured. The thickness of the sealing materials of Examples 1 to 9 and Comparative Examples 1 to 3 was set to 30 μm. The results are presented in Table 2.

In Example 1, the measurement was also performed under the conditions of "leaving the sample B to stand for one minute in an atmosphere at room temperature" and under the conditions of "leaving the sample B to stand for one minute in an atmosphere of 80° C.".

<Ion Elution (Electrolyte Membrane Contaminating Properties)>

Deionized water was introduced into a heat-resistant vessel, and an electrolyte membrane having a size of 5 cm×5 cm (manufactured by DuPont Co., NAFION NRE-212) and a sealing material cut into a size of 5 cm×5 cm were immersed. The vessel was introduced into an oven at 95° C., and after a lapse of 200 hours, the electrolyte membrane was taken out from the vessel and was visually inspected to check the presence or absence of coloration. An electrolyte membrane that was not colored was rated as "A", and an electrolyte membrane that was colored in red was rated as "B". The thickness of the sealing materials of Examples 1 to 9 and Comparative Examples 1 to 3 was set to 30 μm. The results are presented in Table 2.

<Ion Elution (Elution Amount)>

50 g of deionized water was introduced into a heat-resistant vessel, about 2 g of a sealing material layer cut into a size of 5 cm×5 cm was introduced therein, and the vessel was heated for 24 hours in an oven at 120° C. The liquid in the vessel was used as a test liquid, and the ion elution amount of ammonium ions or the like was measured by ion chromatography. Thus, the ion content in the sealing material was calculated. The thickness of the sealing materials of Examples 1 to 9 and Comparative Examples 1 to 3 was set to 30 μm. The results are presented in Table 2.

<Theoretical Tg>

The theoretical Tg of the copolymer resin was calculated as the glass transition temperature (Tg) in terms of theoretical calculation based on Fox's Formula. The results are presented in Table 1.

$$1/Tg = W_1/Tg_1 + W_2/Tg_2 + \ldots + W_i/Tg_i + \ldots + W_n/Tg_n \quad \text{(Fox's Formula)}$$

In the Fox's Formula, the glass transition temperature of a homopolymer of each of the monomers that constitute a polymer formed from n kinds of monomers is designated as $Tg_i$ (K), and the mass proportion of each monomer is designated as $W_i$.

The following relationship is established: $W_1 + W_2 + \ldots + W_i + \ldots W_n = 1$.

<Weight Change (Thermally Induced: 10 minutes at 150° C., 60 minutes at 200° C.)>

The weight of a sealing material having a size of 5 cm×5 cm and a thickness of 30 μm was weighed with an electronic balance (the weight obtained at this time is designated as $M_0$), and the weight of the sealing material obtained after heating the sealing material using an oven under the heating conditions of 10 minutes at 150° C. or under the heating conditions of 60 minutes at 200° C. was measured with an electronic balance (the weight obtained at this time is designated as $M_1$). The weight change caused by heating of the sealing material was calculated as the proportion with respect to the initial weight ($100 \times M_1/M_0$).

The results are presented in Table 3.

<Percentage of Water Content>

The percentage of water content of each of the sealing materials of Examples 1 to 9 and Comparative Examples 1 to 3 was obtained by measuring the moisture included in the gas component generated when the sealing material was heated for 10 minutes at 150° C., by the Karl Fischer titration method using a Karl Fischer moisture meter "AQV-7" manufactured by HIRANUMA SANGYO Co., Ltd.

The results are presented in Table 3.

<Hardness>

A sheet constructed from a PET base material (thickness 75 μm) coated with a sealing material (thickness 30 μm) was cut into a size of about 1 cm×2 cm. The hardness of the sample surface on the small piece thus obtained was measured using an ultramicro hardness meter DUH-201S manufactured by SHIMADZU CORPORATION. The measurement conditions were as follows.

Indenter used: triangular pyramid indenter
Test load: 0.5 mN
Loading rate: 0.1500 mN/sec
Load retention time: 10 sec 1. Indentation Depth (μm)

In regard to the hardness measurement described above, the indenter was forced into the sample surface under the test load (mN) mentioned above, and the amount of penetration was designated as the indentation depth (μm).

2. Elastic Modulus (Pa)

In regard to the hardness measurement described above, the indenter was forced into the sample surface under the test load (mN) mentioned above, and the elastic modulus was calculated from the tangent modulus of a loading/unloading curve obtained after a load retention time of 10 seconds.

The results are presented in Table 3.

Example 1

(Synthesis of Copolymer Resin)

In a separable flask having a capacity of 1 liter, a uniform mixed liquid including 200 parts by mass of water containing 0.2% by mass of polyvinyl alcohol; (a) 10 parts by mass of a styrene monomer (ST) and 20 parts by mass of a methyl methacrylate monomer (MMA); (b) 3 parts by mass of a glycidyl methacrylate monomer (GMA); (c) 67 parts by mass of an ethyl acrylate monomer (EA); 0.1 parts by mass of benzoyl peroxide as a polymerization initiator; and a chain transfer agent for molecular weight adjustment was introduced.

The mixed liquid was heated to 70° C. while being stirred in a nitrogen atmosphere, and suspension polymerization was performed for 4 hours. Next, water was excluded from the suspension liquid by decantation. A solid was washed with water while being subjected to suction filtration, water was evaporated, and then the solid was dried in a vacuum at 60° C. Thus, a copolymer resin (resin composition of Example 1) having a percentage of water content of 0.5% or less was obtained.

From the copolymer resin thus obtained, the weight average molecular weight was measured by a method for measuring the weight average molecular weight, and the value was about 300,000. The monomer composition and the molecular weight are presented in Table 1.

(Production of Sheet-Like Sealing Material)

The copolymer resin thus obtained was fused and stirred in methyl ethyl ketone, and thus a composition for forming a sealing material layer was prepared. The composition for forming a sealing material layer was applied and dried on a release-treated polyester film having a thickness of 75 μm, and thus a sealing material layer was formed. The sealing material layer was produced into a layer having a thickness of 30 μm. The drying conditions for the thickness of 30 μm were set to 100° C. and 2 minutes.

Next, a release-treated polyester film having a thickness of 25 μm was pasted on the sealing material layer, and thus a sheet-like sealing material was obtained.

Examples 2 to 9 and Comparative Examples 1 to 3

Resin compositions and sheet-like sealing materials were obtained in the same manner as in Example 1, except that the compositions of raw material monomers of the copolymer resins and the weight average molecular weights of the copolymer resins were adjusted as indicated in Table 1. The weight average molecular weight of each of Examples and Comparative Examples was adjusted using the amount of the chain transfer agent.

TABLE 1

| | Copolymer resin | | | | | | | | Resin composition Content proportion (mass %) | |
|---|---|---|---|---|---|---|---|---|---|---|
| | Monomer composition (mass %) | | | | | | GMA content (eq/kg) | Theoretical Tg (° C.) | Copolymer resin | Glycidyl curing agent |
| | (a) | (b) | (c) | | | | | | | |
| | MMA | ST | GMA | EA | BA | Mw | | | | |
| Example 1 | 20 | 10 | 3 | 67 | — | 30 × 10$^4$ | 0.21 | 7 | 100 | — |
| Example 2 | 20 | 10 | 3 | 67 | — | 52 × 10$^4$ | 0.21 | 7 | 100 | — |
| Example 3 | 20 | 10 | 3 | — | 67 | 42 × 10$^4$ | 0.21 | −13 | 100 | — |
| Example 4 | 20 | 20 | 3 | 57 | — | 35 × 10$^4$ | 0.21 | 18 | 100 | — |
| Example 5 | 10 | 10 | 3 | 77 | — | 65 × 10$^4$ | 0.21 | −3 | 100 | — |
| Example 6 | — | 20 | 3 | 77 | — | 55 × 10$^4$ | 0.21 | −3 | 100 | — |
| Example 7 | — | 40 | 3 | 57 | — | 30 × 10$^4$ | 0.21 | 17 | 100 | — |
| Example 8 | 20 | 10 | 3 | 67 | — | 52 × 10$^4$ | 0.21 | 7 | 95 | 5 |
| Example 9 | 20 | 10 | 6 | 64 | — | 50 × 10$^4$ | 0.42 | 10 | 100 | — |
| Comparative Example 1 | 20 | 10 | — | 70 | — | 50 × 10$^4$ | — | 6 | 100 | — |
| Comparative Example 2 | 20 | — | 3 | 77 | — | 80 × 10$^4$ | 0.21 | −2 | 100 | — |
| Comparative Example 3 | 45 | — | 3 | 10 | 42 | 80 × 10$^4$ | 0.21 | 12 | 100 | — |

※In Table 1, MMA represents methyl methacrylate; ST represents styrene; GMA represents glycidyl methacrylate; EA represents ethyl acrylate; and BA represents butyl acrylate.

TABLE 2

| | Initial adhesive force (peeling strength) (N/m) | | Adhesive force after enduring hot water (peeling strength) (N/m) | | Ion elution | | | | | | | |
|---|---|---|---|---|---|---|---|---|---|---|---|---|
| | | | | | Electrolyte membrane contamination | Elution amount (ppm/g) | | | | | | |
| | Room temperature | 80° C. | Room temperature | 80° C. | | NH$_4$ | Cl | Na | K | Mg | Li | Ca |
| Example 1 | 784 | 263 | 553 | 238 | A | <1 | <1 | <1 | <1 | <1 | <1 | <1 |
| Example 2 | 836 | 218 | 926 | 274 | A | <1 | <1 | <1 | <1 | <1 | <1 | <1 |
| Example 3 | 546 | 107 | 481 | 109 | A | <1 | <1 | <1 | <1 | <1 | <1 | <1 |
| Example 4 | 501 | 309 | 666 | 205 | A | <1 | <1 | <1 | <1 | <1 | <1 | <1 |
| Example 5 | 689 | 113 | 785 | 199 | A | <1 | <1 | <1 | <1 | <1 | <1 | <1 |
| Example 6 | 952 | 129 | 556 | 147 | A | <1 | <1 | <1 | <1 | <1 | <1 | <1 |
| Example 7 | 965 | 310 | 560 | 413 | A | <1 | <1 | <1 | <1 | <1 | <1 | <1 |
| Example 8 | 644 | 333 | 798 | 365 | A | <1 | <1 | <1 | <1 | <1 | <1 | <1 |
| Example 9 | 494 | 156 | 618 | 361 | A | <1 | <1 | <1 | <1 | <1 | <1 | <1 |
| Comparative Example 1 | 797 | 246 | Peeling NG | Peeling NG | A | <1 | <1 | <1 | <1 | <1 | <1 | <1 |
| Comparative Example 2 | 538 | 52 | 469 | 48 | A | <1 | <1 | <1 | <1 | <1 | <1 | <1 |
| Comparative Example 3 | 57 | 12 | 89 | 10 | A | <1 | <1 | <1 | <1 | <1 | <1 | <1 |

In regard to the evaluation of adhesive force, in Example 1, the peeling strength obtained after leaving the sample A to stand for 50 hours in an atmosphere at room temperature in connection with evaluation of the initial adhesive force was 784 N/m, and the peeling strength obtained after leaving the sample B to stand for 50 hours in an atmosphere at 80° C. was 263 N/m. Furthermore, in regard to the evaluation of enduring hot water, the peeling strength obtained after leaving the sample A to stand for 50 hours in an atmosphere at room temperature was 553 N/m, and the peeling strength obtained after leaving the sample B to stand for 50 hours in an atmosphere at 80° C. was 238 N/m.

TABLE 3

| | Percentage of water content (%) | Weight change (Weight retention ratio) (%) | | Hardness | |
|---|---|---|---|---|---|
| | | 150° C. 10 min | 200° C. 60 min | Indentation depth (μm) | Elastic modulus (Pa) |
| Example 1 | 0.15 | 99.4 | 99.0 | 4.5 | 5.0E+07 |
| Example 2 | 0.16 | 99.4 | 99.0 | 4.8 | 2.3E+07 |
| Example 3 | 0.10 | 99.7 | 99.2 | 9.5 | 8.6E+06 |
| Example 4 | 0.15 | 99.1 | 99.1 | 1.3 | 2.2E+08 |
| Example 5 | 0.14 | 99.5 | 99.4 | 7.2 | 2.2E+07 |
| Example 6 | 0.08 | 99.5 | 99.2 | 6.6 | 2.6E+07 |
| Example 7 | 0.10 | 99.4 | 99.2 | 1.3 | 2.0E+08 |
| Example 8 | 0.16 | 99.4 | 98.6 | 2.6 | 1.1E+08 |
| Example 9 | 0.21 | 99.4 | 99.1 | 6.0 | 1.0E+07 |
| Comparative Example 1 | 0.17 | 99.4 | 98.9 | 4.6 | 2.6E+07 |
| Comparative Example 2 | 0.12 | 99.4 | 99.3 | 8.4 | 8.1E+06 |
| Comparative Example 3 | 0.14 | 99.5 | 99.4 | 2.4 | 5.4E+07 |

From the results of Tables 2 and 3, the sheet materials of Examples 1 to 9 exhibited excellent adhesive force to a m-PPE resin sheet, which is a non-polar material, and also exhibited excellent adhesive force even after a hot water durability treatment (immersion in hot water at 95° C. for 100 hours). Furthermore, according to the evaluation results of Example 1, the sheet materials exhibited excellent adhesive force even after being left to stand for 50 hours at room temperature or at 80° C. after press bonding, and even after being left to stand for 50 hours at room temperature or at 80° C. after the hot water durability treatment.

It can be also confirmed that the sheet materials of Examples 1 to 9 do not exhibit elution of ions. Furthermore, it can be confirmed that as the amount of the component (a) increases, hardness of the resin composition increases.

REFERENCE SIGNS LIST

10: Cell
11: Electrolyte membrane
12, 13: Electrode
14, 15: Separator
14a, 15a: Gas flow channel
16: Sealing material

The invention claimed is:

1. A solid polymer fuel cell sealing material being formed from a resin composition comprising a copolymer resin having a weight average molecular weight of 150,000 or more and formed by copolymerizing raw material components including: (a1) 5% by mass or more of styrene; and (b) 20% by mass or less of glycidyl (meth)acrylate, wherein the copolymer resin is included at a proportion of 50% by mass or more of the total solid content of the resin composition.

2. The solid polymer fuel cell sealing material according to claim 1, wherein the raw material components further include (a2) 5% by mass or more of methyl methacrylate.

3. The solid polymer fuel cell sealing material according to claim 1, wherein the content of glycidyl (meth)acrylate of the copolymer resin is 0.007 to 1.05 eq/kg.

4. The solid polymer fuel cell sealing material according to claim 1, wherein the raw material components further include (c) one or more of other polymerizable monomers selected from a hydroxyalkyl (meth)acrylate or an alkyl (meth)acrylate.

5. The solid polymer fuel cell sealing material according to claim 4, wherein the resin composition further includes a curing agent having a functional group capable of reacting with a glycidyl group.

6. The solid polymer fuel cell sealing material according to claim 1, wherein the copolymer resin is included at a proportion of 60% by mass or more of the total solid content of the resin composition.

7. The solid polymer fuel cell sealing material according to claim 1, wherein the copolymer resin is included at a proportion of 80% by mass or more of the total solid content of the resin composition.

8. The solid polymer fuel cell sealing material according to claim 1, wherein the copolymer resin is included at a proportion of 90% by mass or more of the total solid content of the resin composition.

9. The solid polymer fuel cell sealing material according to claim 1, wherein the solid polymer fuel cell sealing material is in a solid particulate form.

10. The solid polymer fuel cell sealing material according to claim 1, wherein the solid polymer fuel cell sealing material is in a solid sheet-like form.

11. A solid polymer fuel cell sealing material comprising: a sheet-like sealing material layer formed from a resin composition comprising a copolymer resin having a weight average molecular weight of 150,000 or more and formed by copolymerizing raw material components including: (a1) 5% by mass or more of styrene; and (b) 20% by mass or less of glycidyl (meth)acrylate; and peelable base materials respectively disposed on either surface of the sealing material layer to sandwich the sealing material layer.

12. The solid polymer fuel cell sealing material according to claim 11, wherein the raw material components further include (a2) 5% by mass or more of methyl methacrylate.

13. The solid polymer fuel cell sealing material according to claim 11, wherein the content of glycidyl (meth)acrylate of the copolymer resin is 0.007 to 1.05 eq/kg.

14. The solid polymer fuel cell sealing material according to claim 11, wherein the raw material components further include (c) one or more of other polymerizable monomers selected from a hydroxyalkyl (meth)acrylate or an alkyl (meth)acrylate.

15. The solid polymer fuel cell sealing material according to claim 14, wherein the resin composition further includes a curing agent having a functional group capable of reacting with a glycidyl group.

16. The solid polymer fuel cell sealing material according to claim 11, wherein the copolymer resin is included at a proportion of 50% by mass or more of the total solid content of the resin composition.

17. The solid polymer fuel cell sealing material according to claim 11, wherein the copolymer resin is included at a proportion of 60% by mass or more of the total solid content of the resin composition.

18. The solid polymer fuel cell sealing material according to claim 11, wherein the copolymer resin is included at a proportion of 80% by mass or more of the total solid content of the resin composition.

19. The solid polymer fuel cell sealing material according to claim 11, wherein the copolymer resin is included at a proportion of 90% by mass or more of the total solid content of the resin composition.

* * * * *